United States Patent [19]

Konno et al.

[11] Patent Number: 5,767,381
[45] Date of Patent: Jun. 16, 1998

[54] CENTRIFUGE MODEL TEST APPARATUS

[75] Inventors: Takao Konno; Masaharu Sugano, both of Ibaraki-ken; Yuji Tadano, Tsuchiura, all of Japan

[73] Assignee: Hitachi, Ltd., Tokyo, Japan

[21] Appl. No.: 794,230

[22] Filed: Jan. 30, 1997

[30] Foreign Application Priority Data

Jan. 31, 1996 [JP] Japan .................................. 8-014996

[51] Int. Cl.[6] .................................................. G02L 25/00
[52] U.S. Cl. ........................... 73/1.87; 73/865.3; 494/20
[58] Field of Search ............................ 73/1.87, 865.3, 73/865.6, 866.4; 494/17, 20

[56] References Cited

U.S. PATENT DOCUMENTS

| | | | |
|---|---|---|---|
| 2,834,541 | 5/1958 | Szent-gyorgyi et al. | 494/17 |
| 3,011,333 | 12/1961 | Roth et al. | 73/865.3 |
| 3,420,437 | 1/1969 | Blum et al. | 494/20 |
| 3,877,634 | 4/1975 | Rohde et al. | 494/20 X |
| 3,951,334 | 4/1976 | Fleming et al. | 494/20 |
| 4,431,423 | 2/1984 | Weyant, Jr. | 494/20 |
| 4,435,169 | 3/1984 | Romanauskas | 494/20 |
| 4,446,716 | 5/1984 | Fishman | 73/1.87 |
| 5,045,047 | 9/1991 | Hutchins et al. | 494/20 X |

*Primary Examiner*—Elizabeth L. Dougherty
*Attorney, Agent, or Firm*—Antonelli, Terry, Stout & Kraus, LLP

[57] ABSTRACT

A centrifuge model test apparatus is accommodated in a pit, and comprises a vertical rotary shaft, a rotary arm horizontally secured to the rotary shaft, a swing bucket suspended from and supported at a pin on the rotary arm and located near the end thereof so as to be movable in the radial direction of the rotary arm or fixed, and a drive unit for rotating the rotary shaft. As the drive unit is driven and the rotational speed of the rotary shaft increases, the swing bucket is raised together with a sample contained therein due to the centrifugal force with the pin as a center and is placed at a nearly horizontal position when a predetermined rotational speed is reached. A partitioning plate provided under the swing bucket is moved upwards at the time when the swing bucket is raised, and the volume and surface area of the space defined by the partitioning plate and the pit reduce, and the frictional force due to the resistance of the air decreases. This makes it possible to increase the radius of the rotary arm or the load weight on the sample without increasing the driving force. As the rotary arm is made of high damping and easily welded material, vibration caused by resonance can be reduced when the testing apparatus of the centrifuge model is operated with a vibration generating device installed in the testing apparatus.

21 Claims, 3 Drawing Sheets

CENTRIFUGE MODEL TEST APPARATUS

BACKGROUND OF THE INVENTION

The present invention relates to a centrifuge model test apparatus. More specifically, the invention relates to a test apparatus for centrifuge model to testing the strength of a structure by using a reduced-scale model of the structure built on the ground.

When it is attempted to test the strength of a sample by using a reduced-scale model of the building that is built on the ground, it is difficult to reproduce a stress field caused by the self weight in an ordinary gravitational field. In the centrifuge model test apparatus, a bucket for mounting a container containing a reduced-scale model of the structure is suspended from an end of a rotary arm, and the rotary arm is rotated at a high speed. Therefore, a centrifugal acceleration is imparted to the reduced-scale model. The magnitude of the acceleration is N times of a prototype in a model of a 1/N scale.

Prior art related to of a centrifuge model test apparatus of this type includes Japanese Utility Model Publication No. 61-46439/1986, Japanese Patent Laid-Open No. 64-3533/1989 and Japanese Patent Laid-Open No. 4-13946/1992.

The conventional centrifuge model test apparatus has been constituted as described below. A swing bucket is supported at a fulcrum formed by a pin that is provided on the rotary arm and is suspended from the rotary arm and allowed to swing. A test container is placed on the swing bucket. Driving force of a drive unit is transmitted to the rotary arm through a bevel speed change device and a rotary shaft, so that the rotary shaft rotates. As the rotary arm rotates, the swing bucket mounting the test container is swung up around the pin as a fulcrum, and centrifugal acceleration is imparted to the swing bucket.

FIG. 4 illustrates a distribution of the centrifugal acceleration acting on the test container 9. An equal centrifugal acceleration is imparted to points on an arc with the axis of rotation as a center. Ideally, the centrifugal acceleration should be imparted to the sample placed in the test container 9, in such a way that the direction of the centrifugal acceleration is infinitely close to parallel with the bottom surface of the test container 9. For this purpose, the radius r of rotation of the sample must be increased.

To achieve the above requirements, the radius of rotation of the rotary arm should be increased. However, an increase in the radius of rotation of the rotary arm results in an increase in the frictional resistance between the rotary arm and the air and, hence, in an increase in the loss of power.

In addition, the reduced-model is shaken with some hundreds Hertz in a shaking test and a cold rolled-steel used in the rotary arm etc. has poor damping characteristics. It may generate a big vibration, when a shaking frequency coincides with an eigen value of the rotary arm and an outer frame even if the rotary arm and the outer frame can support a reaction force. To overcome this insufficiency, the eigen value of the rotary arm and the outer frame can be greater than that of the shaking frequency. In that case, a bigger rotary arm is needed for increasing the stiffness of the rotary arm and it becomes more expensive.

SUMMARY OF THE INVENTION

In dealing with the centrifuge model test apparatus, the object of the present invention is to decrease the loss of power by decreasing the frictional resistance between the air that whirls accompanying the rotary arm and the wall surface of a pit in which is installed the centrifuge model test apparatus. In addition, the rotary arm can be lengthened without increasing the required output of the drive unit.

Another object of the present invention is to avoid noise at the test container in the shaking test since noise influences an accuracy of experiments by pitching.

The above-mentioned object is accomplished by a first embodiment which is concerned with a centrifuge model test apparatus comprising a rotary arm horizontally secured to a vertical rotary shaft, a swing bucket for holding a sample supported by and suspended from the rotary arm so as to swing, and a drive unit for rotating the rotary shaft, wherein a partitioning means is provided under the rotary arm, and a moving means is provided to move the partitioning means up and down.

The above-mentioned object is further accomplished by a second embodiment which is concerned with a centrifuge model test apparatus comprising a rotary shaft provided substantially vertically, a rotary arm substantially horizontally secured to the rotary shaft, a swing bucket suspended from and supported by the rotary arm so as to swing and holding a sample, and a drive unit for rotating the rotary shaft, wherein a partitioning means is provided under the rotary arm, a sealed bucket for holding a fluid is provided under the partitioning means, and a fluid feed source to feed a fluid is provided to the sealed bucket.

The object of the present invention is further accomplished by a third embodiment which is concerned with a centrifuge model test apparatus comprising a rotary shaft which is substantially vertical, a rotary arm substantially horizontally secured to the rotary shaft, a swing bucket for placing a sample and is suspended from and supported by the rotary arm to rotate in the direction of the rotary arm, and a drive unit for rotating the rotary shaft, wherein a lower disk and an upper disk are arranged at a lower portion and an upper portion of the rotary shaft, and the lower disk is provided with a space control means which, as the rotational speed increases and the swing bucket is raised, reduces space formed between the rotary arm and the lower disk to be smaller than that taken up before the swing bucket is raised, before the rotary arm reaches a predetermined rotational speed.

In any of the above-mentioned embodiments, it is desired that (a) the partitioning means is moved in synchronism with the rotation of the rotary arm, (b) provision is made of a pit for holding at the least the rotary arm and the drive unit, and a cover for covering the pit, (c) the distance between the partitioning means and the rotary arm is shortened to be smaller than the distance set before the rotary arm is rotated before the rotational speed of the rotary arm reaches a predetermined value, and (d) a bucket-moving means is provided to move the swing bucket along the rotary arm. In the first embodiment, (e) moving means for moving the partitioning means up and down is a servo jack. In the second embodiment, (f) the sealed bucket is made of a flexible material, a fluid is poured into the bucket to move the partitioning means upwards, and the fluid is discharged from the bucket to lower the partitioning means. In the first and second embodiments, furthermore, (g) the diameter of the rotary arm is set to be from 2 m to 7 m.

In any of the above-mentioned embodiments, when the same centrifugal acceleration is to be imparted to the test container, the angular rotational speed of the rotary arm decreases with an increase in the length of the rotary arm, but the radius of the pit increases and the frictional resistance increases between the pit and the wall surface. The frictional resistance Df of the rotary arm on the side surface of the pit varies in proportion to the surface area of the side surface of the pit as will be described later. By decreasing the depth of the pit (length in the vertical direction), therefore, the frictional resistance can be decreased.

That is, in a state where the swing bucket is raised accompanying the rotation of the rotary arm, space formed under the rotary arm is decreased to decrease the frictional resistance and, hence, to suppress an increase in the required output of the drive unit.

Further, the above-mentioned object is accomplished by a forth embodiment of the present invention which is concerned with a centrifuge model test apparatus comprising a rotary arm horizontally secured to a vertical rotary shaft, a swing bucket for holding a sample suspended from and supported by the rotary arm so as to swing, and a drive unit for rotating the rotary shaft, wherein said rotary arm is made of Fe—Ni—Mn alloy and the alloy has an austenic phase and a ferritic phase. Preferably, the alloy is comprised of austenic phase, ferritic phase and quasi stable phase.

Other objects, advantages and novel features of the present invention will become apparent from the following detailed description of the invention when considered in conjunction with the accompanying drawings.

DETAILED DESCRIPTION OF THE DRAWINGS

Figure 1:
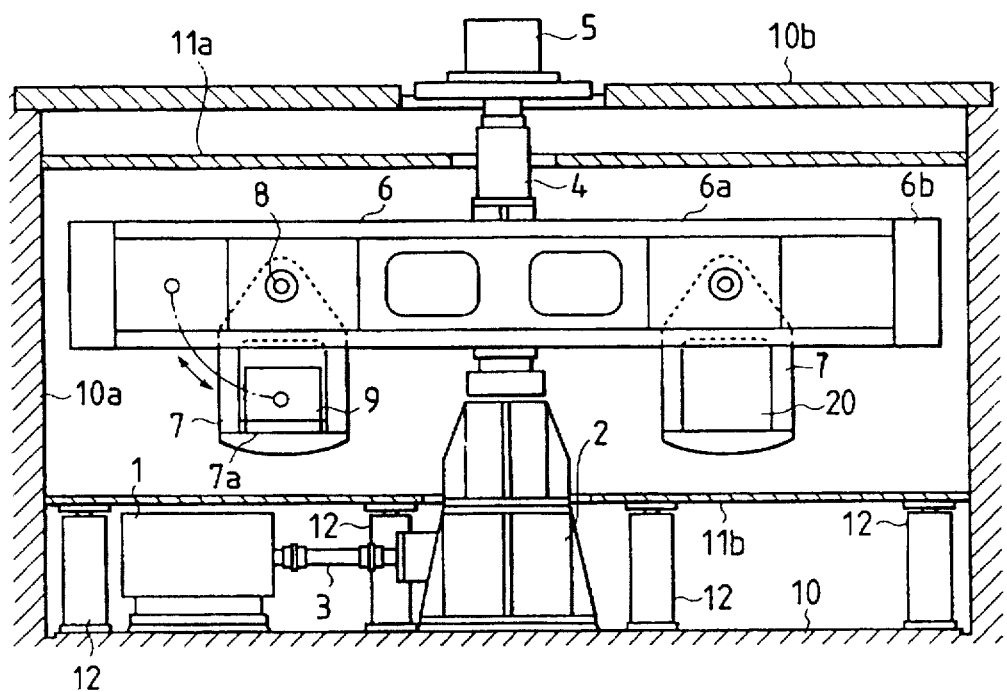
FIG. 1 is a side view of an embodiment of the centrifuge model test apparatus according to the present invention in a state where the rotary arm is at rest.
Figure 2:
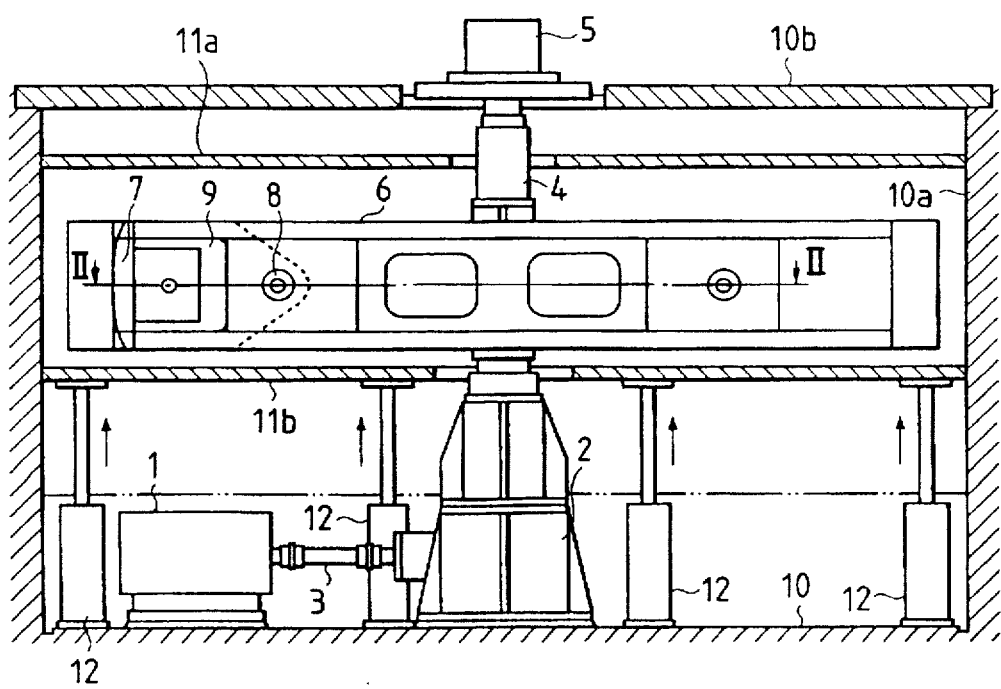
FIG. 2 is a side view of the embodiment of the centrifuge model test apparatus according to the present invention when the rotary arm has reached a predetermined rotational speed.

FIGS. 1 and 2 are side views of an embodiment of the test apparatus of the centrifuge model test apparatus according to the present invention. FIG. 1 illustrates a state before the testing where the rotary arm is at rest, and FIG. 2 illustrates a state where the rotary arm has reached a predetermined rotational speed and a predetermined centrifugal acceleration is imparted to the sample.

In these drawings, a drive unit 1 is installed on the floor surface of a pit that will be described later, and is coupled to a bevel speed change device 2 via a shaft 3. The bevel speed change device 2 is installed on the floor surface of the pit, and an end of the rotary shaft 4 is firmly coupled to the bevel speed change device 2, so that the rotary shaft 4 rotates together with the bevel speed change device 2. The other end of the rotary shaft 4 is supported by a bearing 5 attached to the upper structure and is allowed to rotate. A rotary arm 6 is constructed by welding a structural angle or a plate member, and is firmly attached to the rotary shaft 4 so as to rotate accompanying the rotation of the rotary shaft 4, and receives the rotational drive force from the rotary shaft 4. A swing bucket 7 is suspended from the rotary arm 6 at a pin 8 so as to swing, and is raised or is lowered in the direction of an arrow in FIG. 1 accompanying the rotation of the rotary arm 6. The swing buckets 7, 7 are attached to the rotary arm 6 at right and left positions which are nearly symmetrical with respect to the rotary shaft 1. In one swing bucket 7 is held a test container 9, and in the other swing bucket 7 is held a balance weight 20. The weight of the balance weight 20 has been set to be equal to the total weights of the swing bucket 7 and the test container 9 which are being rotated at a predetermined speed, and the balance weight 20 maintains a balance with respect to the load of the swing bucket 7 and the test container when the rotary arm 6 is being rotated.

The test container 9 contains a sample to be tested, for example, a reduced-scale model of a building built on the ground. During the tests, the water is supplied from a water feeding device that is not shown to adjust the softness of the ground. The pit 10 is constructed under the ground for installing the load testing apparatus that utilizes a centrifugal force, and its side surface 10a maintains a gap so that the end of the rotary arm 6 will not come into contact therewith while it is rotating. A lid 10b is mounted on the pit 10. During the testing, the lid 10b is kept closed to prevent danger. The lid 10b may be constructed as a unitary structure with the pit 10, and an entrance may be formed in the upper surface or in the side surface of the pit 10 so that persons who conduct the tests are allowed to enter into, or come out from, the pit 10.

An upper disk 11a is provided over the rotary arm 6 in the pit 10 maintaining a gap so that the rotary arm 6 being rotated will not come in contact therewith. A lower disk 11b is provided under the rotary arm 6, and is caused to move up and down owing to the expansion or contraction of servo jacks 12. As the swing buckets 7 are raised in a horizontal direction accompanying an increase in the rotational speed of the rotary arm 6, space formed relative to the rotary arm 6 is adjusted by moving the lower disk 11b up or down.

In the above-described embodiment, a support member 6a and the outer frame 6b of the rotary arm 6, the swing bucket 7 and the test container 9 deform elastically when they are shaken. Therefore they were made by welding process. They preferably have high tensile strength, to be able to weld, to be easily processed and to have high damping characteristics. These needs are met with Fe—Ni—Mn alloys, especially alloys that have eutectoid of an austenic phase, a ferritic phase, and a quasi stable phase. The quasi stable phase is not always needed. The alloy may be stainless steel such that its surface is porous. The porous surface is made by melting off materials that are along intercrystals or near them. This alloy is obtained by dipping a stainless steel in a liquid acid of high temperature for predetermined time, after elongations the crystals of the stainless steel. The above-mentioned needs are also met with SS41 steel (general rolled steel) that is processed by flattening the surfaces after roughing the 12 surfaces.

Figure 3:
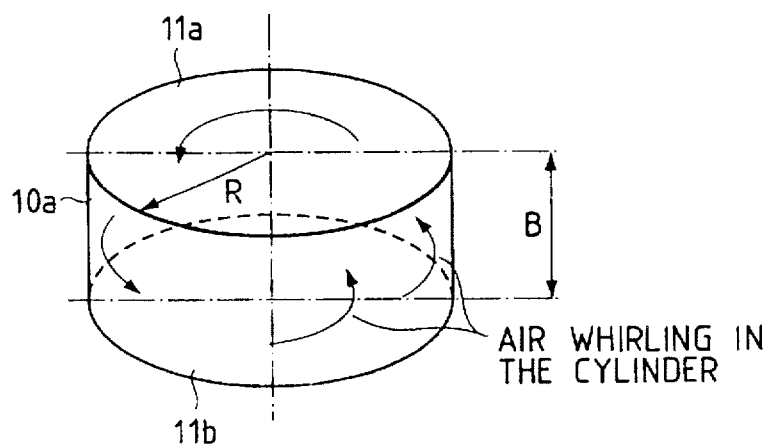
FIG. 3 is a diagram illustrating the flow of the air rotating with the rotary arm of the centrifuge model.

Described below is how to operate the thus constituted testing apparatus. When the drive unit 1 is rotated (at about 160 rpm), the rotational drive force is transmitted to the rotary shaft 4 via the bevel shaft 3 and speed change device 2, and the rotary arm 6 rotates accompanying the rotation of the rotary shaft 4. As the rotary arm 6 rotates and a centrifugal force is imparted to the swing bucket 7, the test container 9 secured onto the swing bucket 7 is raised with the pin 8 as a center in proportion to the rise in the rotational speed of the rotary arm 6 (raised horizontally). Thus, the centrifugal force in the circumferential direction is exerted on the sample in the test container 9. In this case, the air in the pit 10 accommodating the testing apparatus whirls together with the rotary arm 6 as shown in FIG. 3. Frictional resistance (wind loss resistance) is produced with respect to the rotary arm 6 as the flow of the air is disturbed by the side surface 10a of the pit 10, upper disk 11a and lower disk 11b.

As described above, the lower disk 11b is supported by a plurality of servo jacks 12 from the lower side. A control unit that is not shown gives an instruction to the servo jacks 12 to narrow the space under the rotary arm 6 in response to an increase in the rotational speed of the rotary arm 6 before the rotary arm 6 reaches the predetermined rotational speed, and the servo jacks 12 gradually raise the lower disk 11b in response to the instruction. The lower disk 11b withstands the weight of the persons who mount the test container 9 to conduct the tests. When the rotational speed of the rotary arm 6 decreases after having finished the predetermined testing, the swing bucket 7 is lowered in a direction indicated by arrow, and the lower disk 11b is lowered by the servo jacks 12 so as not to come into contact with the swing bucket 7.

Described below are the reasons why the frictional force can be decreased and the required output of the drive unit 1 need not be increased.

From the length $r_a$ of the rotary arm and the rotational speed N, the centrifugal acceleration $\alpha$ imparted to the test container 9 is expressed by the following formula, $$\alpha = r_a \cdot \omega^2 \quad (1)$$

where $$\omega = N \cdot 2\pi/60 \quad (2)$$

Figure 4:
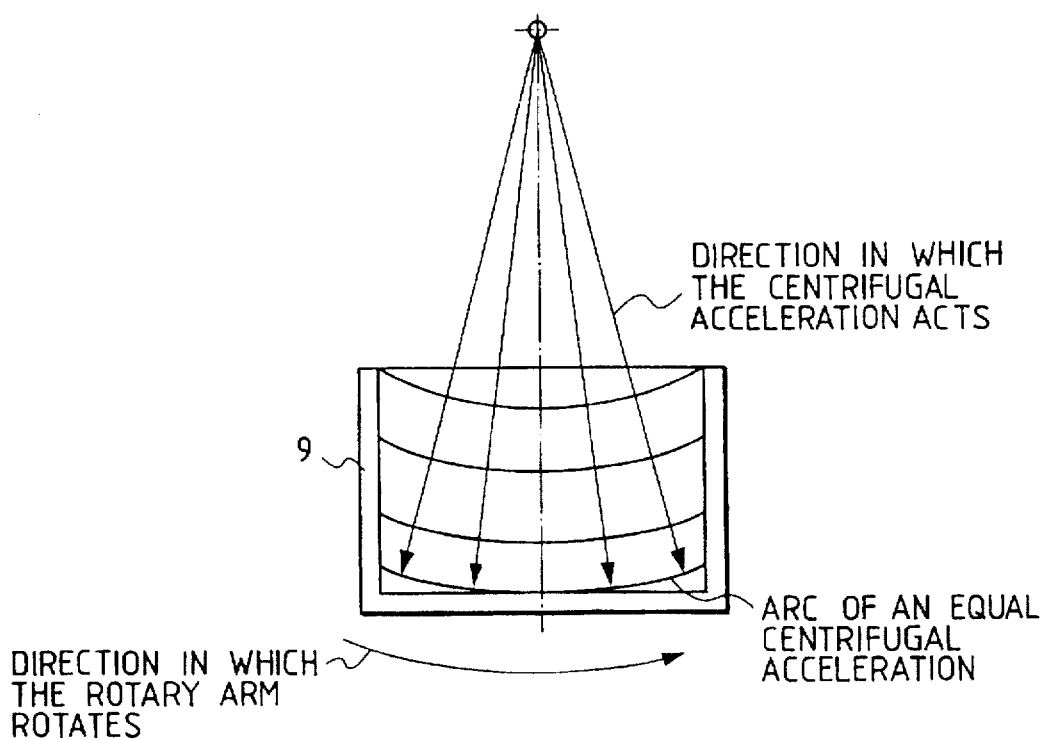
FIG. 4 is a diagram explaining a distribution of the centrifugal acceleration imparted to the test container, and is a sectional view along II—II of FIG. 2.

To rotate the rotary arm 6 at the rotational speed N, the drive unit 1 must produce an output larger than the wind loss. The rotary arm 6 has a large radius of rotation and is installed in the cylindrical pit. To construct the pit at a reduced cost, the size of the pit 10 is not so much larger than the rotary arm 6. As shown in FIG. 4, therefore, the wind loss can be modeled as the frictional resistance acting between the wall surface 10a of the pit 10 and the air whirling accompanying the rotation of the rotary arm 6.

In this case, the frictional resistance is generated by the side surface 10a of the pit 10, by the upper disk 11a and by the lower disk 11b, and is expressed in the following way.

(I) Frictional resistance Df on the side surface 10a

If the velocity of the fluid is V (m/sec), surface area is F (m$^2$), density of the fluid is $\rho$(kg/m$^3$) and coefficient of frictional resistance is $Cf_1$, then, the frictional resistance Df is expressed as, $$Df = Cf_1 \cdot (\rho/2) \cdot V^{2 \cdot F} \quad (3)$$

$$F = L \cdot B \quad (4)$$

If the radius of the pit 10 is R (m), the length in the direction of flow is L ($=2\pi R$) (m), and the depth of the pit 10 is B (m), then, $$V = r_a \cdot \omega \quad (5)$$

(II) Resistance torque $M_2$ received by one surface of either the upper disk 11a or the lower disk 11b In compliance with the formula of the friction of the disk rotating in a fluid, the resistance torque $M_2$ is expressed as, $$M_2 = (1/2) \cdot \rho \cdot \omega^2 \cdot R^5 \cdot (0.6 \cdot Cf_2) \quad (6)$$

Therefore, the drive unit 1 must produce an output Pm, $$Pm >> (P_1 + P_2) \quad (7)$$

$$P_1 = R \cdot Df \cdot N \cdot (1/974)$$

$$P_2 = 2 \cdot M_2 \cdot N \cdot (1/974)$$

In order that a plane with a constant centrifugal acceleration imparted to the sample in the bucket is brought to be in parallel with the bottom surface of the test container 9 and is uniformed infinitely, the rotary arm 6 must have an increased length $r_a$. In this case, the pit 10 for installing the testing apparatus of the centrifuge model must have an increased radius R, and the drive unit 1 must produce an increased output Pm according to the formulas (3), (4), (6) and (7). From the formula (3), the frictional resistance Df on the side surface 10a of the pit varies in proportion to the surface area F. In the formula (4), therefore, the frictional resistance Df can be decreased by decreasing the depth B of the pit 10 to suppress the required output Pm of the drive unit 1 expressed by the formula (7).

In the centrifuge model testing apparatus, when a maximum value of the centrifugal acceleration $\alpha$ is set to be 200G (G: gravitational acceleration), it is desired that the diameter of the rotary arm 6 is set to be from 2 to 7 m from the standpoint of economy in constructing the apparatus. When the diameter is smaller than 2 m, the usual gravitational field cannot be approximated, which is not desirable (see FIG. 4). When the diameter is larger than 7 m, on the other hand, the testing can be conducted approximating the usual gravitational field resulting, however, the increased power loss since in rotary arm 6 is lengthened. Moreover, the rotary arm 6 must have an increased structural strength requiring an increased manufacturing cost, which is not economically desirable.

According to this embodiment, the space under the rotary arm 6 is reduced as the rotary arm 6 rotates, and the frictional resistance Df due to the air is decreased on the side surface 10a of the pit. Therefore, the drive unit need not produce an increased output, and it is possible to easily lengthen the rotary arm 6.

Figure 5:
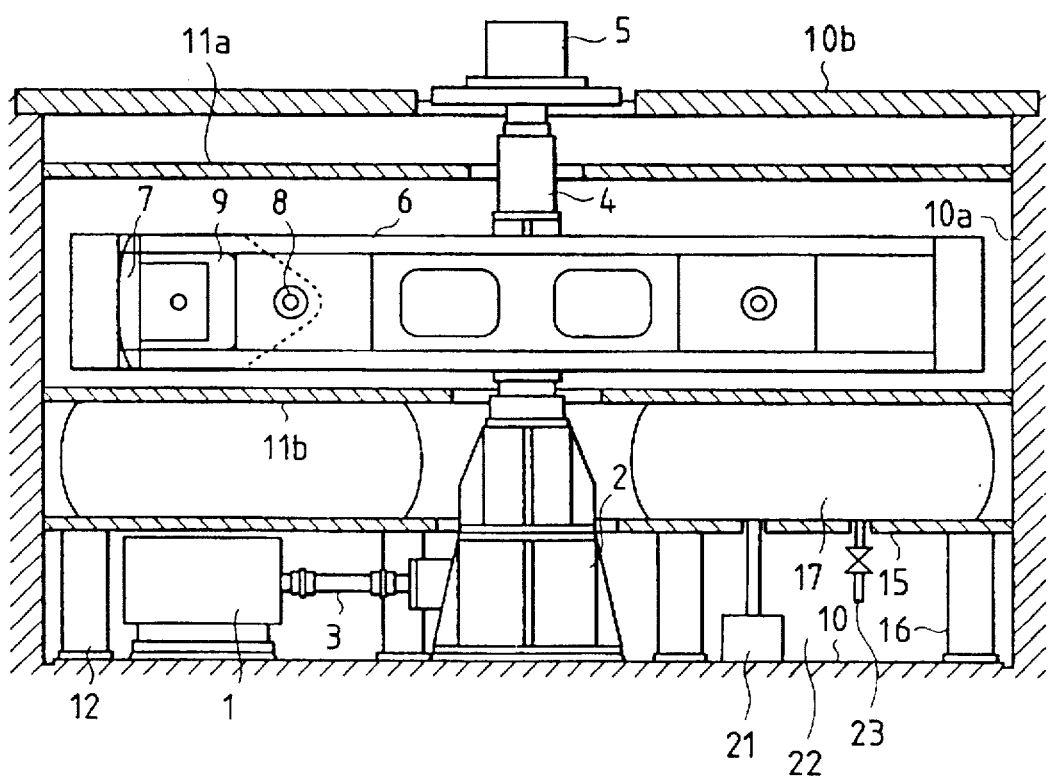
FIG. 5 is a side view of another embodiment of the centrifuge model test apparatus according to the present invention when the rotary arm has reached a predetermined rotational speed.

FIG. 5 illustrates another embodiment of the centrifuge model test apparatus in a state where the rotary arm 6 has reached a predetermined rotational speed.

A floor board 15 is arranged on the drive unit 1 installed in the pit 10, and is secured on a plurality of bed plates 16. Bags 17 are made of an elastic material such as rubber and inflate as a fluid is introduced therein under the application of pressure. The bags 17 are placed between the floor board 15 and the upper plate 18, and are connected to a fluid source 21 having a pump or a compressor. The bags 17 have a discharge port 23 formed via a valve 22. The floor board 15 serves as a scaffold at the time when the persons who conduct the tests mount the test container 9 on the swing bucket 7, and is hence firmly constructed to withstand the weight of the persons who conduct the tests.

Described below is the operation of the thus constituted centrifuge model testing apparatus. When the drive unit 1 is rotated, the rotational force is transmitted to the rotary shaft 4 via the bevel speed change device 2, then the rotary arm 6 rotates. As the centrifugal force is imparted to the swing bucket 7 accompanying the rotation of the rotary arm 6, the swing bucket 7 is tilted in proportion to an increase in the rotational speed of the rotary arm 6 with the pin 8 as a center, and an acceleration in the circumferential direction is imparted to the test container 9 placed on the swing bucket 7. In this case, the air in the pit 10 whirls accompanying the rotation of the rotary arm 6 as shown in FIG. 3, and acts as the frictional resistance among the side surface 10a of the pit 10, upper disk 11a and floor plate 15. This is the same as that of the embodiment shown in FIGS. 1 and 2.

As the swing bucket 7 rises in proportion to an increase in the rotational speed of the rotary arm 6, increased space is formed under the rotary arm 6. Therefore, a fluid is supplied from the fluid feed source to the bags 17 to inflate the empty bags 17. As the empty bags 17 inflate, the floor board 15 rises being pushed by the bags 17. Therefore, the space under the rotary arm 6 becomes small, and the frictional resistance decreases. After the test is finished, the fluid is discharged through discharge ports formed in the bags 17.

In this embodiment, the control mechanism for raising and lowering the lower disk 11b mounted on the bags 17 is simplified compared with that of the embodiment shown in FIG. 1, and the control reliability is improved.

In the above-mentioned embodiments, or the lower disk or the floor plate which is the partitioning means provided under the rotary arm is rotated in synchronism with the rotary arm. However, the rotation of the rotary arm needs not be necessarily brought into synchronism with the motion of the partitioning means. When the partitioning means is at least moving while the rotary arm is rotating, the frictional resistance decreases due to a decrease in space under the rotary arm, which is the effect specific to the present invention.

In the above-mentioned embodiments, furthermore, the position from the center of rotation of the arm 6 is fixed. In order to change the centrifugal load, however, the position in the radial direction may be changed. Even in this case, a gap must be maintained so that the swing bucket that is raised up to nearly the horizontal position will not come into contact with the side surface of the pit. By providing a control means for changing the position in the radial direction depending upon the rotational speed of the rotary arm, it is possible to conduct the tests with further increased precision. The control device may be provided on the rotary arm or inside or outside of the pit.

According to the present invention as will be obvious from the aforementioned embodiments, the space around the rotary arm becomes small while the rotary arm is rotating to decrease the frictional resistance that occurs between the side surface of the pit and the air around the rotary arm. Therefore, the drive unit need not produce an increased output and the rotary arm can be lengthened.

When a shaker 7a shakes the swing bucket 7 installed in the shaker 7a, resonance of the swing bucket 7, the test container 9 and the outer frame 6b may be generated because they are elastically deformed. According to the present invention, this resonance is suppressed owing to the damping of the materials and the elastic deformation is reduced. Thus, the bad vibration that effects the test results of the pitching behavior of the test container 9 is reduced.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A centrifuge model test apparatus comprising a rotary arm horizontally secured to a vertical rotary shaft, a swing bucket for holding a sample suspended from and supported by the rotary arm so as to swing, a drive unit for rotating the rotary shaft, a partitioning means provided under the rotary arm, and a moving means to move the partitioning means up and down so as to reduce a distance between said partitioning means and said rotary arm when a rotational speed of said rotary arm increases.

2. A centrifuge model test apparatus according to claim 1, wherein said partitioning means is moved in synchronism with the rotation of said rotary arm.

3. A centrifuge model test apparatus according to claim 1, further comprising a pit for accommodating at least said rotary arm and said drive unit, and a cover for covering said pit.

4. A centrifuge model test apparatus according to claim 1, wherein a distance between said partitioning means and said rotary arm is shortened to be smaller than that set before the rotary arm is rotated, before the rotational speed of said rotary arm reaches a predetermined value.

5. A centrifuge model test apparatus according to claim 1, wherein the moving means for moving said partitioning means up and down is a servo jack.

6. A centrifuge model test apparatus according to claim 1, wherein a bucket-moving means is provided to move said swing bucket along said rotary arm.

7. A centrifuge model test apparatus according to claim 1, wherein said rotary arm is made by welding and made of steel that is able to weld and has high damping characteristics.

8. A centrifuge model test apparatus according to claim 7, wherein said rotary arm is made of a Fe—Ni—Mn alloy and the alloy has an austenic phase and a ferritic phase.

9. A centrifuge model test apparatus comprising a rotary shaft provided substantially vertically, a rotary arm substantially horizontally secured to the rotary shaft, a swing bucket suspended from a supported by the rotary arm so as to swing and holding a sample, a drive unit for rotating the rotary shaft, a partitioning means provided under the rotary arm, a sealed bucket for holding a fluid is provided under the partitioning means, and a fluid feed source to feed a fluid is provided to the sealed bucket to inflate the sealed bucket and raise the partitioning means so as to reduce a distance between said partitioning means and the rotary arm when a rotational speed of the rotary arm increases.

10. A centrifuge model test apparatus according to claim 9, wherein said partitioning means is moved in synchronism with the rotation of said rotary arm.

11. A centrifuge model test apparatus according to claim 9, further comprising a pit for accommodating at least said rotary arm and said drive unit, and a cover for covering said pit.

12. A centrifuge model test apparatus according to claim 9, wherein a distance between said partitioning means and said rotary arm is shortened to be smaller than that set before the rotary arm is rotated, before the rotational speed of said rotary arm reaches a predetermined value.

13. A centrifuge model test apparatus according to claim 9, wherein a bucket-moving means is provided to move said swing bucket along said rotary arm.

14. A centrifuge model test apparatus according to claim 9, wherein said sealed bucket is made of a flexible material, and said partitioning means is moved upwards by pouring a fluid into the sealed bucket and is moved downwards by discharging the fluid from said sealed bucket.

15. A centrifuge model test apparatus according to claim 1, wherein said rotary arm has a diameter of from 2 m to 7 m.

16. A centrifuge model test apparatus according to claim 9, wherein said rotary arm has a diameter of from 2 m to 7 m.

17. A centrifuge model test apparatus comprising a rotary shaft which is substantially vertical, a rotary arm substantially horizontally secured to the rotary shaft, a swing bucket for placing a sample suspended from and supported by the rotary arm to rotate in the direction of the rotary arm, a drive unit for rotating the rotary shaft, a lower disk and an upper disk arranged respectively at a lower portion and an upper portion of the rotary shaft, and space control means connected to the lower disk for, as the rotational speed increases and the swing bucket is raised, decreasing space formed between the rotary arm and the lower disk to be smaller than that taken up before the swing bucket is raised, before the rotary arm reaches a predetermined rotational speed.

18. A centrifuge model test apparatus comprising a rotary arm horizontally secured to a vertical rotary shaft, a swing bucket for holding a sample suspended from and supported by the rotary arm so as to swing, a drive unit for rotating the rotary shaft, and partitioning means provided under the rotary arm, wherein the partitioning means moves vertically so as to reduce a distance between the partitioning means and the rotary arm when a rotational speed of the rotary arm increases, and wherein said rotary arm is made of a Fe—Ni—Mn alloy and the alloy has an austenic phase, a ferritic phase and a quasi stable phase.

19. A centrifuge model test apparatus, comprising a vertically extending rotary shaft;

a horizontally and longitudinally extending rotary arm connected at a middle portion thereof to the rotary shaft;

a swing bucket for holding a test sample, having a pivot connection to the rotary arm, the swing bucket being pivotable between a rest position hanging vertically from the pivot connection below the rotary arm and an operating position in which the swing bucket extends horizontally from the pivot connection towards an end of the rotary arm away from the rotary shaft;

a drive unit for rotating the rotary shaft and the rotary arm and for imparting centrifugal force to the swing bucket to raise the swing bucket from the rest position to the operating position;

a circumferential, vertical side surface surrounding the test apparatus;

an upper partition provided over and spaced from the rotary arm;

a lower disk provided under and spaced from the rotary arm and extending radially from adjacent said rotary shaft to said circumferential, vertical side surface, the lower disk being vertically movable; and a control unit for controlling movement of the lower disk to raise the lower disk in response to an increase in rotational speed of the rotary arm to decrease the space between the rotary arm and the lower disk as the swing bucket pivots to the operating position and to lower the lower disk in response to a decrease in rotational speed of the rotary arm to increase the space between the rotary arm and the lower disk as the swing bucket pivots to the rest position, whereby a frictional resistance of the rotary arm can be decreased during operation by reducing the surface area surrounding the rotary arm.

20. A centrifuge model test apparatus according to claim 19, wherein the rotary arm has a length of 2 m to 7 m.

21. A centrifuge model test apparatus according to claim 19, further comprising an additional swing bucket for holding a balance weight, the additional swing bucket having a pivot connection to the rotary arm at a position nearly symmetrical to the position of the swing bucket with respect to the rotary shaft.

* * * * *